United States Patent
Gaffney et al.

(10) Patent No.: US 10,987,403 B2
(45) Date of Patent: Apr. 27, 2021

(54) CYCLODEXTRIN-NLE3-A(1-7) COMPOSITIONS AND THEIR USE

(71) Applicants: Kevin J. Gaffney, Los Angeles, CA (US); Stan G. Louie, Fullerton, CA (US); Kathleen E. Rodgers, Long Beach, CA (US)

(72) Inventors: Kevin J. Gaffney, Los Angeles, CA (US); Stan G. Louie, Fullerton, CA (US); Kathleen E. Rodgers, Long Beach, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/491,042

(22) PCT Filed: Mar. 9, 2018

(86) PCT No.: PCT/US2018/021645
§ 371 (c)(1),
(2) Date: Sep. 4, 2019

(87) PCT Pub. No.: WO2018/165495
PCT Pub. Date: Sep. 13, 2018

(65) Prior Publication Data
US 2020/0009212 A1    Jan. 9, 2020

Related U.S. Application Data

(60) Provisional application No. 62/469,969, filed on Mar. 10, 2017.

(51) Int. Cl.
*A61K 38/08* (2019.01)
*A61K 47/40* (2006.01)
(Continued)

(52) U.S. Cl.
CPC .......... *A61K 38/085* (2013.01); *A61K 9/0053* (2013.01); *A61K 47/40* (2013.01); *A61K 47/6951* (2017.08); *A61P 7/00* (2018.01)

(58) Field of Classification Search
CPC ...... A61K 38/085; A61K 47/40; A61K 47/61; C07K 7/14
See application file for complete search history.

(56) References Cited

U.S. PATENT DOCUMENTS

| | | | | |
|---|---|---|---|---|
| 2005/0277595 | A1* | 12/2005 | Rodgers | A61K 38/085 424/85.2 |
| 2012/0302505 | A1* | 11/2012 | Fetzer | A61K 38/08 514/15.4 |
| 2013/0183367 | A1* | 7/2013 | Souza dos Santos | A61P 5/00 424/450 |

FOREIGN PATENT DOCUMENTS

| | | |
|---|---|---|
| WO | 2013/119870 | 8/2013 |
| WO | 2014/179440 | 11/2014 |
| WO | 2015/057403 | 4/2015 |

OTHER PUBLICATIONS

Horsky et al. Inclusion Complexes of Proteins: Interaction of Cyclodextrins with Peptides Containing Aromatic Amino Acids Studied by Competitive Spectrophotometry. Journal of Inclusion Phenomena and Molecular Recognition in Chemistry. 1994, vol. 18, pp. 291-300. (Year: 1994).*

(Continued)

*Primary Examiner* — Jeffrey E. Russel
(74) *Attorney, Agent, or Firm* — McDonnell Boehnen Hulbert & Berghoff LLP

(57) ABSTRACT

Disclosed herein are compositions including cyclodextrin and Nle3-A(1-7) [Asp-Arg-Me-Tyr-Ile-His-Pro (SEQ ID NO: 1)] and their use in treating various disorders.

12 Claims, 3 Drawing Sheets

Specification includes a Sequence Listing.

Days post chemotherapy

(51) Int. Cl.
A61K 47/69 (2017.01)
A61P 7/00 (2006.01)
A61K 9/00 (2006.01)

(56) References Cited

OTHER PUBLICATIONS

The International Search Report (ISR) with Written Opinion for PCT/US2018/021645 dated Jun. 11, 2018, pp. 1-29.
Lula, Ivana et al. "Study of angiotensin-(1-7) vasoactive peptide and its β-cyclodextrin inclusion complexes: Complete sequence-specific NMR assignments and structural studies" Peptides (2007) vol. 28, pp. 2199-2210.
Fraga-Silva, Rodrigo Araujo et al. "An orally active formulation of angiotensin-(1-7) produces an antithrombotic effect" Clinics (2011) vol. 66(5), pp. 837-841.
Marques, Fú'lvia D. et al. "An Oral Formulation of Angiotensin-(1-7) Produces Cardioprotective Effects in Infarcted and Isoproterenol-Treated Rats" Hypertension (2011) vol. 57(3), pp. 477-483.
Heringer-Walther, Silvia et al. "Angiotensin-(1-7) stimulates hematopoietic progenitor cells in vitro and in vivo" Haematologica (2009) vol. 94(6), pp. 857-860.
Rodgers, Kathleen E. et al. "NorLeu3-Angiotensin (1-7) [DSC127] as a Therapy for the Healing of Diabetic Foot Ulcers" Advances in Wound Care (2015) vol. 4(6), pp. 339-345.
Machado-Silva, Alice et al. "Therapeutic uses for Angiotensin-(1-7)" Expert Opinion on Therapeutic Patents (2016) vol. 26(6), pp. 669-678.
Frezard, Frederic et al. "Nanocarriers for Improved Delivery of Angiotensin-(1-7)", The Protective Arm of the Renin Angiotensin System, Elsevier (2015), pp. FP1-FP3.

* cited by examiner

CYCLODEXTRIN-NLE3-A(1-7) COMPOSITIONS AND THEIR USE

RELATED APPLICATIONS

This application is a U.S. national phase of International Application No. PCT/2018/021645, filed on Mar. 9, 2018, which claims priority to U.S. Provisional Application No. 62/469,969, filed Mar. 10, 2017, both of which are incorporated by reference herein in their entirety.

BACKGROUND OF THE INVENTION

The renin angiotensin system (RAS) is known for its role in regulating and maintaining hemodynamic parameters, in particular blood pressure. Since its initial discovery, RAS has been found to play a role in a variety of other biological systems including wound healing and hematopoiesis. The recognition that there are two arms in the RAS system, referred to as the classical arm and protective arm, has further enhanced our understanding. Angiotensin II (AII) was first described as a vasoconstrictive peptide where its binding onto its cognate receptor, AT1R, will activate and maintain inflammation after tissue injury. In contrast, angiotensin (1-7) (A(1-7)) opposes AII-mediated inflammation and promotes tissue repair and progenitor cell mobilization through its binding to the Mas receptor.

Investigational Mas agonists peptides, A(1-7) and Nor-Leu3 angiotensin (1-7) (NorLeu3A(1-7)) can be administered either topically or parenterally. Systemic administration of Mas agonist is currently achieved through daily subcutaneous (SQ) administration, which can compromise adherence especially if these compounds are chronically administered.

SUMMARY OF THE DISCLOSURE

In one aspect the disclosure provides compositions comprising cyclodextrin and a peptide comprising or consisting of Nle3-A(1-7) [Asp-Ara-Nle-Tyr-Ile-His-Pro (SEQ ID NO: 1)] or a pharmaceutically acceptable salt thereof. In one embodiment, the cyclodextrin and the peptide are covalently linked. In another embodiment, the composition comprises an Nle3-A(1-7) inclusion complex. In various embodiments, the cyclodextrin and peptide are present in a molar ratio of between about 1:1 and 10:1, between about 1:1 and 5:1, or are present in a molar ratio about 1:1. In a further embodiment, the peptide is present at a concentration of between about 0.05 µg/mg (w/w) and about 1 mg/mg (w/w).

In another aspect, the disclosure provides pharmaceutical compositions comprising:

(a) the composition of any embodiment or combination of embodiments of the disclosure: and (b) a pharmaceutically acceptable carrier.

In a further aspect are disclosed methods for treating a subject, comprising orally administering to a subject an amount effective of the cyclodextrin-peptide inclusion complex of any embodiment or combination of embodiments of the disclosure or the pharmaceutical composition of embodiment or combination of embodiments of the disclosure to treat a disorder that may benefit from treatment with a peptide comprising or consisting of Nle3-A(1-7) or a pharmaceutically acceptable salt thereof. In one embodiment, the subject will be undergoing, is undergoing or has undergone chemotherapy, radiation therapy, and/or bone marrow transplantation. In another embodiment, the subject has chemotherapy induced myelosuppression and/or myelodysplastic syndrome (MDS). In a further embodiment, the methods are used to treat and/or limit damage to mucosal tissue in the subject. In a further embodiment, the subject has a gastrointestinal disease, including but not limited to Crohn's disease and irritable bowel syndrome. In one embodiment, the subject has a disorder selected from the group consisting of diabetes, multiple sclerosis (MS), or muscular dystrophy (MD). In a further embodiment, the subject is less than 18 years of age.

DETAILED DESCRIPTION OF THE DISCLOSURE

Figure 1:
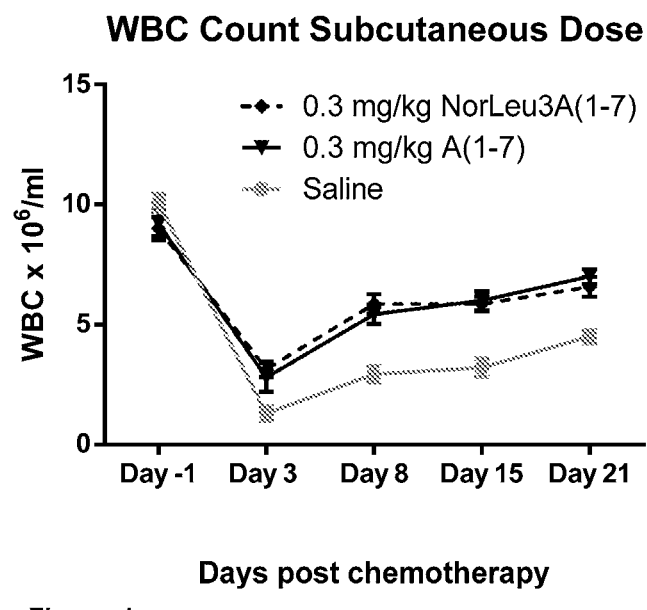
FIG. 1. Graph depicting white blood cell counts for mice at baseline (day −1) and clays 3, 8, 15, and 21 post gemcitabine treatment. Mice were dosed with gemcitabine on day 0, began daily subcutaneous treatment with saline, A(1-7), or NorLeu3A(1-7) on day 1, and were treated for 21 days.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, the term "about" means+/−5% of the recited parameter.

In one aspect are provided compositions comprising cyclodextrin and a peptide comprising or consisting of Nle3-A(1-7) [Asp-Arg-Nle-Tyr-Ile-His-Pro (SEQ ID NO:1)] or a pharmaceutically acceptable salt thereof. As disclosed in the example that follows, the inventions have unexpectedly discovered that the claimed compositions, when administered orally, are significantly more potent than corresponding A(1-7) compositions or corresponding subcutaneous formulations of Nle3-A(1-7). Such a finding would not have been expected by those of skill in the art.

Cyclodextrins are a family of compounds made up of sugar molecules bound together in a ring (cyclic oligosaccharides). Cyclodextrins are composed of 5 or more α-D-glucopyranoside units linked 1→4. Typical cyclodextrins contain a number of glucose monomers ranging from six to eight units in a ring, creating a cone shape. Any suitable cyclodextrin may be used. In one embodiment, the cyclodextrin is selected from the group consisting of β-cyclodextrin (seven sugar ring molecule), α-cyclodextrin (six membered sugar ring molecule), γ-cyclodextrin (eight sugar ring molecule), randomly methylated beta cyclodextrin, hydroxypropyl beta cyclodextrin, and modifications thereof. In one specific embodiment, the cyclodextrin comprises β-cyclodextrin.

In one embodiment, the cyclodextrin and the peptide are covalently linked. In other embodiments, the cyclodextrin and the peptide are not covalently linked. In one embodiment, the composition comprising an Nle3-A(1-7) inclusion complex. As used herein, an inclusion complex means that the peptide comprising or consisting of Nle3-A(1-7) is at least partially inserted into the cavity of one cyclodextrin molecule. Furthermore, a peptide may at least partially be inserted into the cavity of more cyclodextrin molecules, and two moieties of a single peptide may each be inserted into one cyclodextrin molecule to give 1:2 ratio between cyclodextrin and peptide. Thus, the complex may be termed as an inclusion complex (Clathrate) between the cyclodextrin and the peptide. Similarly, the complex may comprise more than one peptide molecule at least partially inserted into one or more cyclodextrin molecules, wherein for example 2 peptide molecules are at least partially inserted into a single cyclodextrin molecule, to give a 1:2 ratio between cyclodextrin and peptide.

Any suitable molar ratio of cyclodextrin to peptide can be used. In one embodiment, the molar ratio of cyclodextrin to peptide is at least 1:1; in various further embodiments, the molar ratio of cyclodextrin to peptide is between about 1:1 and 10:1, 1:1 and 9:1, 1:1 and 8:1, 1:1 and 7:1, 1:1 and 6:1, 1:1 and 5:1, 1:1 and 4:1, 1:1 and 3:1, 1:1 and 2:1, or about 1:1. In specific embodiments, the molar ratio of cyclodextrin to peptide may be between about 1:1 to about 2:1, about 1:1, or about 2:1.

Any suitable amount of the peptide or a pharmaceutically acceptable salt thereof may be present in the composition, such as an effective dosage form of the peptide for an intended use. In one embodiment, the amount of peptide or a pharmaceutically acceptable salt thereof present in the composition is at least 0.05 mg/mg (w/w). In various further embodiments, the peptide or a pharmaceutically acceptable salt thereof is present at a concentration of between about 0.05 μg/mg (w/w) and about 500 μg/mg (w/w), between about 0.05 μg/mg (w/w) and about 100 μg/mg (w/w), between about 0.05 μg/mg (w/w) and about 50 μg/mg (w/w), between about 0.05 μg/mg (w/w) and about 25 μg/mg (w/w), between about 0.05 μg/mg (w/w) and about 10 μg/mg (w/w); between about 0.05 μg/mg (w/w) and about 5 μg/mg (w/w), between about 0.05 μg/mg (w/w) and about 1.0 μg/mg (w/w), between about 0.05 μg/mg (w/w) and about 0.5 μg/mg (w/w), or between about 0.05 μg/mg (w/w) and about 0.1 μg/mg (w/w) of the total composition.

In another aspect are provided pharmaceutical compositions comprising the composition or inclusion complex of any embodiment or combination of embodiments of the disclosure, and a pharmaceutically acceptable carrier.

In all aspects of the invention, the peptide, or salt thereof may be administered (or present in the pharmaceutical compositions) together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The peptides may be administered with a lyoprotectant, e.g. sucrose, sorbitol or trehalose. In certain embodiments, the peptides may be administered with a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the peptides may be administered with a bulking agent, like glycine. In yet other embodiments, the peptides may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The peptides may be administered with a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the peptides may be administered with a stabilizer, e.g., a molecule which, when combined with the peptide substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride, paraben, and combinations of methyl paraben and propyl paraben.

In all aspects and embodiments of the disclosure, suitable acids which are capable of forming salts with the peptide include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptide include, but are not limited to, inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The peptide or salt thereof can further be derivatized to provide enhanced half-life, for example, by linking to polyethylene glycol. The peptide therapeutic or salt thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties.

The peptide or salt thereof may be the sole active agent in the pharmaceutical composition, or the composition may further comprise one or more other active agents as desired for a given purpose.

Any suitable dosage form may be used for delivery of the pharmaceutical compositions of the invention, as may be suitable for any given use of the pharmaceutical composition. In non-limiting embodiments, the dosage form is formulated into a form selected from the group consisting of tablets, gelcaps, softgels, and capsules for oral delivery. In another aspect are provided methods for treating a subject, comprising orally administering to a subject an amount effective of the cyclodextrin-peptide composition or inclusion complex or the pharmaceutical composition of any embodiment or combination of embodiments of the disclosure to treat a disorder that may benefit from treatment with a peptide comprising or consisting of Nle3-A(1-7) or a pharmaceutically acceptable salt thereof.

Oral formulations/delivery adds ease of use and convenience compared to injections in systemic diseases including, but not limited to, diabetes, multiple sclerosis (MS), muscular dystrophy (MD), etc. Injections are painful, annoying, the delivery site has to be cleaned, and needles produce dangerous and biohazardous waste.

The subject may be any subject suffering from or at risk of a disorder that may benefit from treatment with a peptide comprising or consisting of Nle3-A(1-7) or a pharmaceutically acceptable salt thereof. For example, the examples show that the disclosed formulations increase circulating white blood cells, platelets, and the number of progenitors in the bone marrow. Thus, any subject with a disorder that would benefit from a treatment that increase circulating white blood cells, platelets, and/or the number of progenitors in the bone marrow can usefully be treated by the methods of the invention. In one embodiment, the subject will be undergoing, is undergoing or has undergone chemotherapy, radiation therapy, and/or bone marrow transplantation. In another embodiment, the subject has chemotherapy induced myelosuppression and or myelodysplastic syndrome (MDS). In a further embodiment, the methods are used to treat and/or limit damage to mucosal tissue in the subject. In one embodiment, the subject has a gastrointestinal disease, including but not limited to Crohn's disease and irritable bowel syndrome. As shown in the examples that follow, the lack of any early reduction in platelets in the studies carried out reflects mucosal healing, such that the compositions can be used for the recited methods where mucosal healing is advantageous. In another embodiment, the subject has a disorder selected from the group consisting of diabetes, multiple sclerosis (MS), or muscular dystrophy (MD).

The subject may be any suitable subject, such as a mammalian subject. In one specific embodiment, the subject is a human subject. In a further embodiment, the human subject is less than 18 years of age. In this pediatric embodiment, the methods obviate the need to provide peptide injections to the child.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the compound (specific activity, etc.), the route of administration, the stage and severity of the disorder, the weight and general state of health of the subject, and the judgment of the prescribing physician. It will be understood that the amount of the inclusion complex or pharmaceutical composition actually administered will be determined by a physician, in the light of the above relevant circumstances.

The compositions of the invention can be administered as the sole active pharmaceutical agent, or they can be used in combination with one or more other compounds useful for carrying out the methods of the invention. When administered as a combination, the other therapeutic agents can be formulated as separate compositions that are given at the same time or different times, or the other therapeutic agents can be given as a single composition with the compositions.

Examples

The renin angiotensin system (RAS) is known for its role in regulating and maintaining hemodynamic parameters, in particular blood pressure. Since its initial discovery, RAS has been found to play a critical role in a variety of other biological systems including wound healing and hematopoiesis. The recognition that there are two arms in the RAS system, referred to as the classical arm and protective arm, has further enhanced our understanding. Angiotensin 11 (AII) was first described as a vasoconstrictive peptide where its binding onto its cognate receptor, AT1R, will activate and maintain inflammation after tissue injury. In contrast, angiotensin (1-7) (A(1-7)) opposes AII-mediated inflammation and promotes tissue repair and progenitor cell mobilization through its binding to the Mas receptor.

These biological activities have led us to evaluate the impact of Mas agonists in two bone marrow diseases: chemotherapy induced myelosuppression and myelodysplastic syndrome (MDS). Investigational Mas agonists peptides, A(1-7) and NorLeu3 angiotensin (1-7) (NorLeu3A(1-7)) can be administered either topically or parenterally. Systemic administration of Mas agonist is currently achieved through daily subcutaneous (SQ) administration. However, daily injections can also compromise adherence especially if these compounds are chronically administered.

We have developed a molecular-encapsulation formulations of Mas agonists, and evaluated in animals to determine their efficacy to reduce chemotherapy associated bone marrow suppression.

Preparation of Inclusion Complexes

To a glass vial filled a 1:1 ratio of β-cyclodextrin (Ashland Product Code: 826760) and NorLeu3A(1-7).Acetate (Peptisyntha S A. Brussels, Belgium) was added a sufficient amount of water (Sigma-Aldrich, Co., St. Louis, Mo.; Product Code; W4502) to produce a 12 mM (based on the millimoles of β-cyclodextrin) solution. After stirring for 2 days at room temperature, the contents of the vial were decanted into a 50 mL conical tube, frozen with liquid nitrogen, and lyophilized overnight yielding a white powder.

2A. Oral Efficacy Study Design and Experimental Methods

The female C57Bl/6 mice (7 per group), 6-8 weeks old, were treated with the formulations described above daily starting 1 day after intravenous injection with chemotherapy, 160 mg/kg gemcitabine. On days 1, 3, 7, 15 and 21 after chemotherapy administration, blood was taken under anesthesia from the saphenous vein to assess white blood cell, and platelet numbers. On day 22, the mice were euthanized and bone marrow collected to assess the number of colony forming units.

Bleeding of Mice

The mice were bled from the saphenous vein. The mice were anesthetized by placing the nose of the animals in a 50 ml conical tube containing cotton balls soaked with isoflurane (an inhaled anesthesia). Once anesthesia was affected, the animals were taken from the tube and held firmly. Approximately 50 µl of blood were obtained from the saphenous vein and collected using a microcuvette microfuge tube containing 10 mM EDTA and held on ice until further processing.

WBC and Platelet Evaluation

Twenty µl of blood was mixed with 180 µl of RBC lysing solution (0.83% NH4Cl, 10 mM EDTA, 0.5% NaHCO3). The mixture was then incubated for 10 minutes at 4° C. After this incubation, the supernatant was removed and the pellet was resuspended in 100 µl of PBS. To this, 100 µl of 0.04% trypan blue was added. This mixture was vortexed and the number of WBC was evaluated by hematocytometer under light microscopy and the number of platelets was evaluated by hematocytometer under phase contrast microscopy.

Evaluation of Myeloid and Erythroid Progenitors in the Bone Marrow

The femurs were collected and the bone marrow was harvested by flushing with PBS containing 2% fetal calf serum and 2× PenStrep™. After collection of the bone marrow, the cells were pelleted at 1,000 rpm at 4° C. for 10 min, resuspended, and the number of nucleated cells were counted using a Z1 Coulter Counter (Beckman Coulter). Aliquots of cells were then resuspended at $5\times10^6$ cells/ml. For each sample, 20 µl portion of each suspension was added to a 24 well plate well containing 980 µl of semisolid medium containing MethoCult™ (Stem Cell Technologies, Vancouver, BC; 0.9% methyl cellulose in Iscove's MDM, 15% fetal calf serum, 1% bovine serum albumin, 10 µg/ml bovine pancreatic insulin, 200 µg/ml human transferrin, $10^{-4}$ M 2-mercaptoethanol, 2 mM glutamine, 10 ng/ml recombinant murine interleukin 3, 10 ng/ml recombinant human interleukin 6, 50 ng/ml recombinant murine stem cell factor and 3 units/ml erythropoietin). The cultures were then placed at 37° C. in a humidified atmosphere of 5% CO2 in air. At day 14, the number of progenitor colonies formed was enumerated under phase contrast microscopy.

Evaluation of Mesenchymal Stem Cell Progenitors in the Bone Marrow

The above cell suspensions were also used to evaluate MSC number. Two mls of Mesencult™ MSC Basal Medium (mouse) supplemented with Mesencult™ MSC Stimulatory Supplement (mouse) (Stem Cell Technologies) were added to each well of a 24 well plate followed by 100 uL of cells from each respective sample. The plates were incubated for 8 days at 37° C. in a humidified atmosphere of 5% CO2 in air. On day 8, the colonies were counted by light microscopy.

2B. Oral Efficacy Study Results

Figure 2:
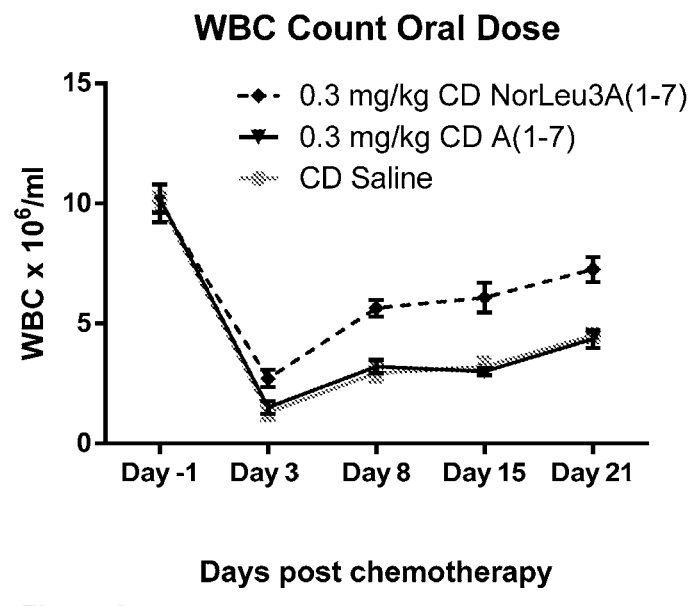
FIG. 2. Graph depicting white blood cell counts for mice at baseline (day −1) and days 3, 8, 15, and 21 post gemcitabine treatment. Mice were dosed with gemcitabine on day 0, began daily oral treatment with cyclodextrin (CD) saline vehicle, CD+A(1-7), or CD+NorLeu3A(1-7) on day 1, and were treated for 21 days.
Figure 3:
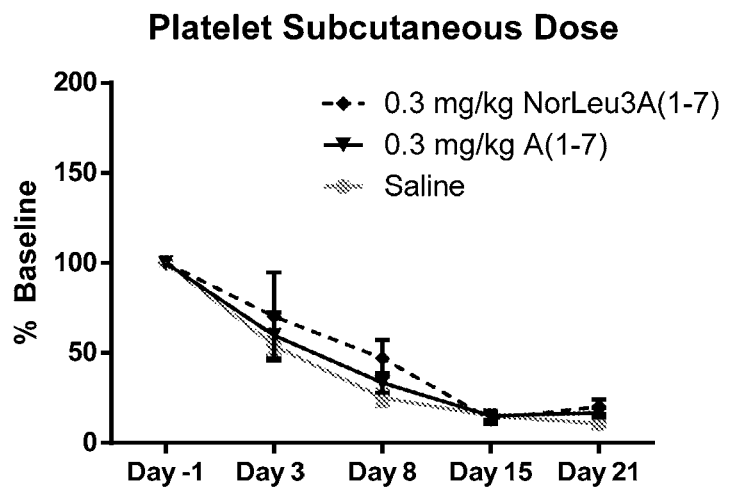
FIG. 3. Graph depicting platelet counts for mice at baseline (day −1) and days 3, 8, 15, and 21 post gemcitabine treatment. Mice were dosed with gemcitabine on day 0, began daily subcutaneous treatment with vehicle, A(1-7), or NorLeu3A(1-7) on day 1, and were treated for 21 days.
Figure 4:
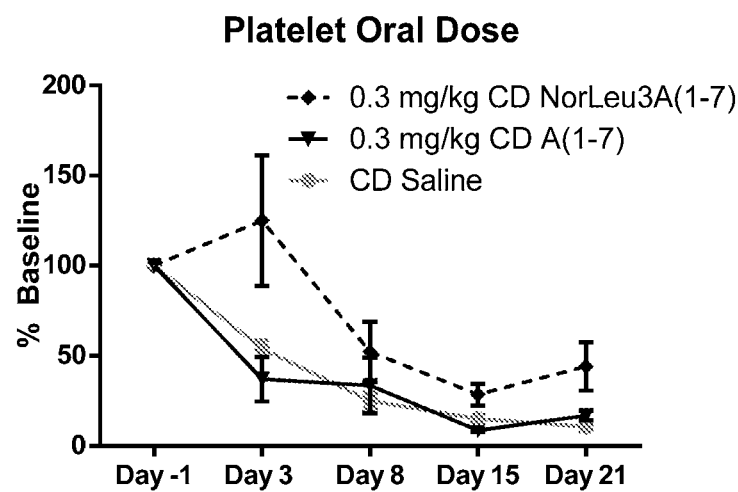
FIG. 4. Graph depicting platelet counts for mice at baseline (day −1) and days 3, 8, 15, and 21 post gemcitabine treatment. Mice were dosed with gemcitabine on day 0, began daily oral treatment with cyclodextrin (CD) saline vehicle, CD+A(1-7), or CD+NorLeu3A(1-7) on day 1, and were treated for 21 days.
Figure 5:
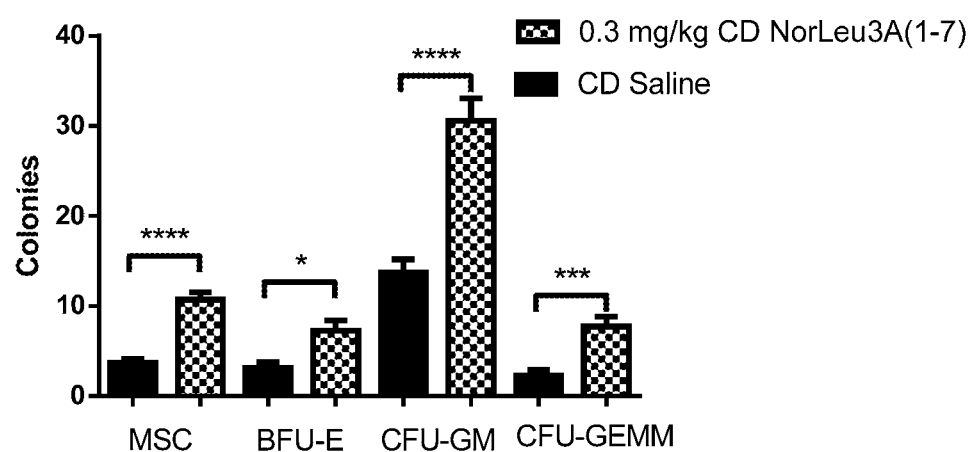
FIG. 5. Graph depicting bone marrow mesenchymal stem cell (MSC), burst forming unit-erythroid (BFU-E), colony-forming unit-granulocyte, erythrocyte and monocyte (CFU-GM), and colony-forming unit-granulocyte, erythrocyte, monocyte, and megakaryocyte (CFU-GEMM) counts in gemcitabine-dosed mice after 21 days of oral cyclodextrin (CD) saline vehicle or CD+NorLeu3A(1-7) treatment. Mice were dosed with gemcitabine on day 0, began daily oral treatment with on day 1, and were treated for 21 days.

In order to assess the oral efficacy, gemcitabine-treated mice were treated daily for 21 days with five treatments: 1) SQ dosed saline, 2) SQ dosed A(1-7) at 0.3 mg/kg, 3) SQ dosed NorLeu3-A(1-7) at 0.3 mg/kg, 4) orally dosed β-CD formulated A(1-7) at 0.3 mg/kg, or 5) orally dosed β-CD formulated NorLeu-A(1-7)) at 0.3 mg/kg. The effects of these treatments on peripheral blood counts were assessed. Subcutaneous injection of both peptides increased the number of circulating WBC (FIG. 1). Orally dosed β-CD formulated NorLeu-A(1-7) increased circulating WBC whereas orally dosed β-CD formulated A(1-7) did not (FIG. 2). Further, orally dosed β-CD formulated NorLeu3-A(1-7) increased circulating platelet numbers (FIG. 4), whereas subcutaneous injection of NorLeu3-A(1-7) did not circulating platelet numbers (FIG. 3). Finally, treatment with orally dosed β-CD formulated NorLeu3-A(1-7) increased the number of progenitors in the bone marrow (FIG. 5).

We claim:

1. A method for treating a subject, comprising orally administering to a subject a composition comprising cyclodextrin and a peptide comprising or consisting of Nle3-A (1-7) [Asp-Arg-Nle-Tyr-Ile-His-Pro (SEQ ID NO:1)], or a pharmaceutically acceptable salt thereof, in an amount effective to treat a disorder that may benefit from treatment with a peptide comprising or consisting of Nle3-A(1-7) or a pharmaceutically acceptable salt thereof, wherein:

(a) the subject will be undergoing, is undergoing or has undergone chemotherapy, radiation therapy, and/or bone marrow transplantation;

(b) the subject has chemotherapy induced myelosuppression and/or myelodysplastic syndrome (MDS); or (c) the subject has a disorder selected from the group consisting of multiple sclerosis (MS) and muscular dystrophy (MD).

2. The method of claim 1, wherein the subject will be undergoing, is undergoing or has undergone chemotherapy, radiation therapy, and/or bone marrow transplantation.

3. The method of claim 1 wherein the subject has chemotherapy induced myelosuppression and/or myelodysplastic syndrome (MDS).

4. The method of claim 1, wherein the subject has a disorder selected from the group consisting of multiple sclerosis (MS) and muscular dystrophy (MD).

5. The method of claim 1, wherein the subject is a human subject.

6. The method of claim 5, wherein the subject is less than 18 years of age.

7. The method of claim 1, wherein the composition comprises an Nle3-A(1-7) inclusion complex.

8. The method of claim 1, wherein the cyclodextrin comprises β-cyclodextrin.

9. The method of claim 1, wherein the cyclodextrin and peptide are present in a molar ratio of between about 1:1 and 10:1.

10. The method of claim 1, wherein the cyclodextrin and peptide are present in a molar ratio of between about 1:1 and 5:1.

11. The method of claim 1, wherein the cyclodextrin and peptide are present in a molar ratio of between about 1:1 and about 2:1.

12. The method of claim 1, wherein the peptide is present at a concentration of between about 0.05 μg/mg (w/w) and about 500 μg/mg (w/w).

* * * * *

```
SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa at position three is Norleucine (Nle)

<400> SEQUENCE: 1

Asp Arg Xaa Tyr Ile His Pro
1               5
```